United States Patent [19]

Rönnberg

[11] Patent Number: 5,674,215

[45] Date of Patent: Oct. 7, 1997

[54] ABSORBENT ARTICLE HAVING SEPARATELY ATTACHED SIDE-FLAPS, AND A METHOD OF MANUFACTURING SUCH AN ARTICLE

[75] Inventor: Peter Rönnberg, Mölndal, Sweden

[73] Assignee: Mölnlycke AB, Gothenburg, Sweden

[21] Appl. No.: 433,464

[22] PCT Filed: Nov. 11, 1993

[86] PCT No.: PCT/SE93/00964

§ 371 Date: Aug. 1, 1995

§ 102(e) Date: Aug. 1, 1995

[87] PCT Pub. No.: WO94/10952

PCT Pub. Date: May 26, 1994

[30] Foreign Application Priority Data

Nov. 11, 1992 [SE] Sweden .................. 9203372

[51] Int. Cl.[6] .................. A61F 13/15; A61F 13/20; B32B 31/08

[52] U.S. Cl. .................. 604/385.2; 604/385.1; 156/164; 156/265

[58] Field of Search .................. 604/385.1–387; 156/161, 163, 164, 229, 259, 264, 265

[56] References Cited

U.S. PATENT DOCUMENTS

| 4,595,441 | 6/1986 | Holvoet et al. .................. 156/265 |
|---|---|---|
| 4,636,207 | 1/1987 | Buell .................. 604/385.2 |
| 4,834,740 | 5/1989 | Suzuki et al. . |
| 5,019,067 | 5/1991 | Simmons . |
| 5,061,261 | 10/1991 | Suzuki et al. . |
| 5,080,658 | 1/1992 | Igaue et al. . |
| 5,246,432 | 9/1993 | Suzuki et al. .................. 604/385.2 |
| 5,292,316 | 3/1994 | Suzuki et al. .................. 604/385.2 |
| 5,330,598 | 7/1994 | Erdman et al. .................. 156/265 |
| 5,344,516 | 9/1994 | Tanji et al. .................. 156/265 |
| 5,391,162 | 2/1995 | Widlund et al. .................. 604/385.2 |

FOREIGN PATENT DOCUMENTS

| 595785 | 4/1990 | Australia . |
|---|---|---|
| 0145080 | 6/1985 | European Pat. Off. . |
| 7412756-4 | 11/1978 | Sweden . |
| 2214057 | 8/1989 | United Kingdom . |
| 2262873 | 7/1993 | United Kingdom . |
| 2271501 | 4/1994 | United Kingdom . |

*Primary Examiner*—Mark O. Polutta
*Attorney, Agent, or Firm*—Burns, Doane, Swecker & Mathis, L.L.P.

[57] ABSTRACT

An absorbent article, particularly a diaper, has a central absorbent unit (1) which is comprised of an elongated absorbent body (2) enclosed between a liquid-permeable inner casing sheet (3) which lies proximal to the wearer in use, and a liquid-impermeable, outer casing sheet (4) which lies distal from the wearer in use. The absorbent unit is provided along its longitudinal edges (9) with liquid-impermeable folds (6) which are upstanding from the inner casing sheet and which form side-leakage barriers. The article has a side-flap (18) on each side of the absorbent unit (1). The side-flaps (18), optionally with associated edge (21, 23), are produced in the form of rectangular strips (10) completely separated from the absorbent unit (1) and are thereafter jointed thereto. A longitudinally extending edge-part (13) of each strip (10) is suitably folded double and the backwardly fold part (19) is joined to the outer casing sheet (3a, 4b or 4) of the absorbent unit (1)along a curved fastening line (21). When the aper is to be used, the side-flaps (18) are pulled-out laterally, the length of this extension, and therewith the width of the resulting side-flaps (18), being dependent on the curved shape of the fastening line (21). It is therewith possible to produce a curved contour (16) of the diaper for conforming to the wearer's legs with side-flaps (18) which originally have straight edges (11) The material from which the side-flaps (18) are made can be chosen quite independently of the inner and the outer casing sheets (3, 4), so as to avoid irritation of the wearer's skin while still fitting closely to the wearer's legs.

15 Claims, 3 Drawing Sheets

ABSORBENT ARTICLE HAVING SEPARATELY ATTACHED SIDE-FLAPS, AND A METHOD OF MANUFACTURING SUCH AN ARTICLE

FIELD OF THE INVENTION

The present invention relates to absorbent articles, such as diapers, incontinence guards, sanitary napkins and like articles, and in particular to an absorbent disposable article.

DISCUSSION OF RELATED ART

The curved outer contour desirable to adapt the side-flaps to the wearer's legs so as to hold the absorbent unit correctly positioned, creates difficulties in manufacture. When the casing-layer starting material is in the form of a web of uniform width, the contour can be produced by clipping away edge-parts. The drawback with this method is the wastage that occurs, this wastage increasing the costs of material and requiring separate handling of the waste to remove it from the clipping station during manufacture. Another problem is encountered when the article is to be provided with edge elastic along its outer contour during the manufacture of the elastic article, since it is difficult to apply elastic elements along a curved line when said elements concerned have the form of relatively broad bands which are to be fastened to one or both surfaces of the side-flaps or between layers included therein.

In order to avoid these problems, it is proposed, for instance, in EP-A2-0,145,080, to form an upstanding fold of a centre part of each long side of a rectangular diaper blank. The folds are folded-in over the absorbent body and glued to the inner casing sheet. In this way, the centre part of the diaper, the crotch part, is given a narrower shape without needing to clip-out the contour. Edge elastic can be applied along the straight edges prior to forming the folds. However, this diaper has the drawback that the effective width of the absorbent body is reduced by the overlying folds, in which the liquid-impermeable outer casing sheet is included. The folds may also cause the diaper to be feel uncomfortable when the diaper is worn.

OBJECT AND SUMMARY

The present invention is intended to avoid the aforesaid problems and to provide an absorbent article which has a curved outer contour when in its position of use and which can be manufactured readily without waste and can be readily provided with broad edge elastic when so desired while, at the same time, avoiding a reduction in the active width of the absorbent body when forming the curved outer contour.

In the case of known diapers that are provided with side-flaps, the sheet material from either the inner or the outer casing sheet of the diaper, or from both sheets, is included in the side-flaps. This causes limitations with regard to the choice of a material that will ensure that the side-flaps do not irritate the wearer's skin and, at the same time, possess the elastic properties desired. Accordingly, a further object of the invention is that the material from which the side-flaps are made can be chosen quite independently of the materials used in the inner and the outer casing sheets.

BRIEF DESCRIPTION OF THE DRAWINGS

The invention will now be described in more detail with reference to the accompanying drawings, in which.

DETAILED DESCRIPTION OF THE PREFERRED EMBODIMENTS

Figure 3:
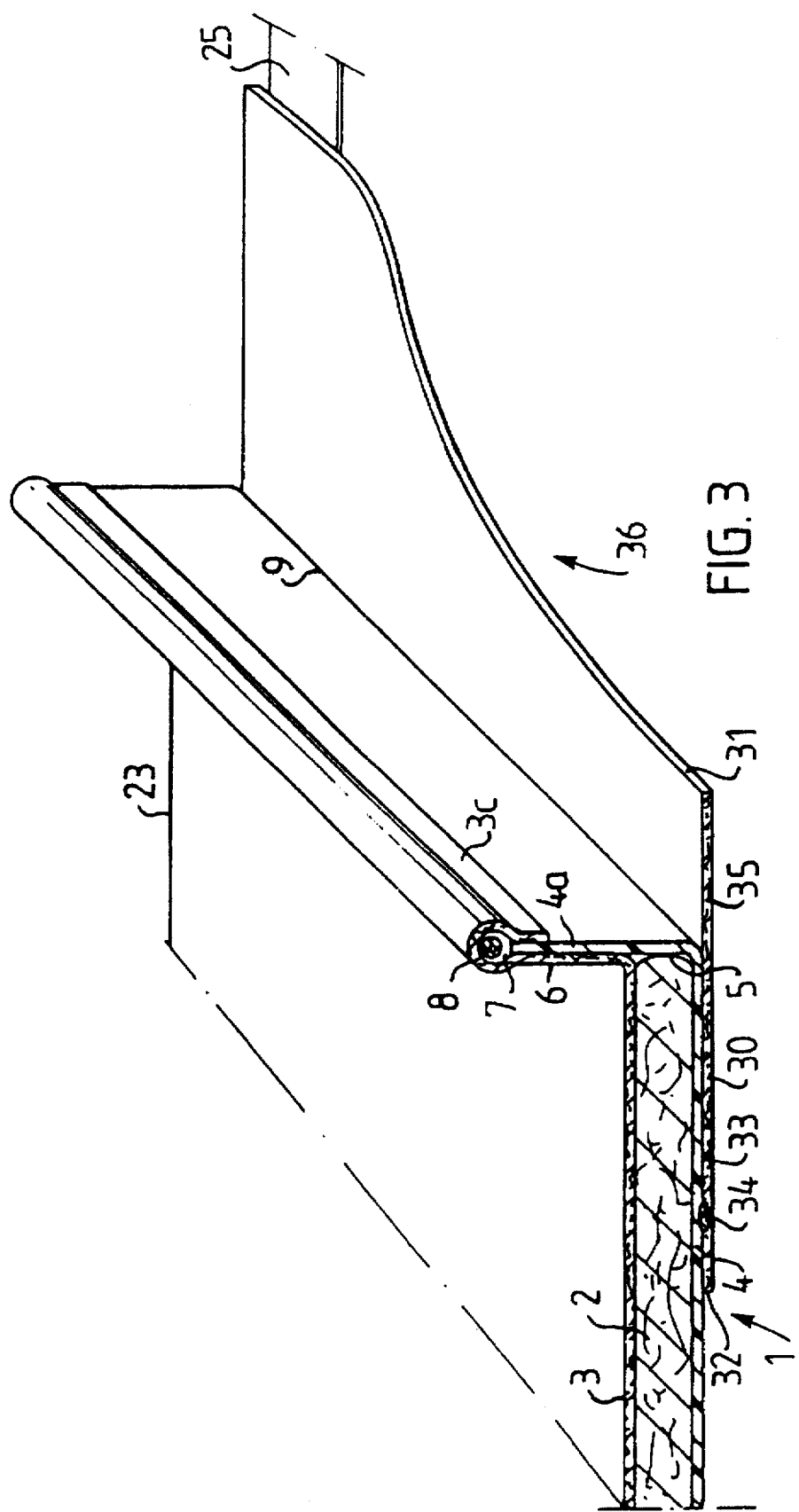

The Figures illustrate a disposable diaper, which has a so-called hourglass shape in its use state. The diaper includes an absorbent unit 1 which comprises an absorbent body 2 which is enclosed between an inner and an outer casing sheet 3 and 4 respectively. The casing sheet 3 is made of a liquid-permeable and soft sheet material, for instance a nonwoven material, and is intended to lie proximal to the wearer in use. The outer casing sheet 4 is made of a liquid-impermeable material, such as plastic sheet for instance. The absorbent body 2 may, for instance, include absorbent fibre material, such as cellulose fluff, to which so-called superabsorbent material has been added. The absorbent body 2 is elongated and has two mutually opposing and mutually parallel longitudinally extending side-edges 5, of which only one is seen in FIGS. 1 and 3 respectively, these Figures essentially showing one-quarter of the diaper.

Figure 1:
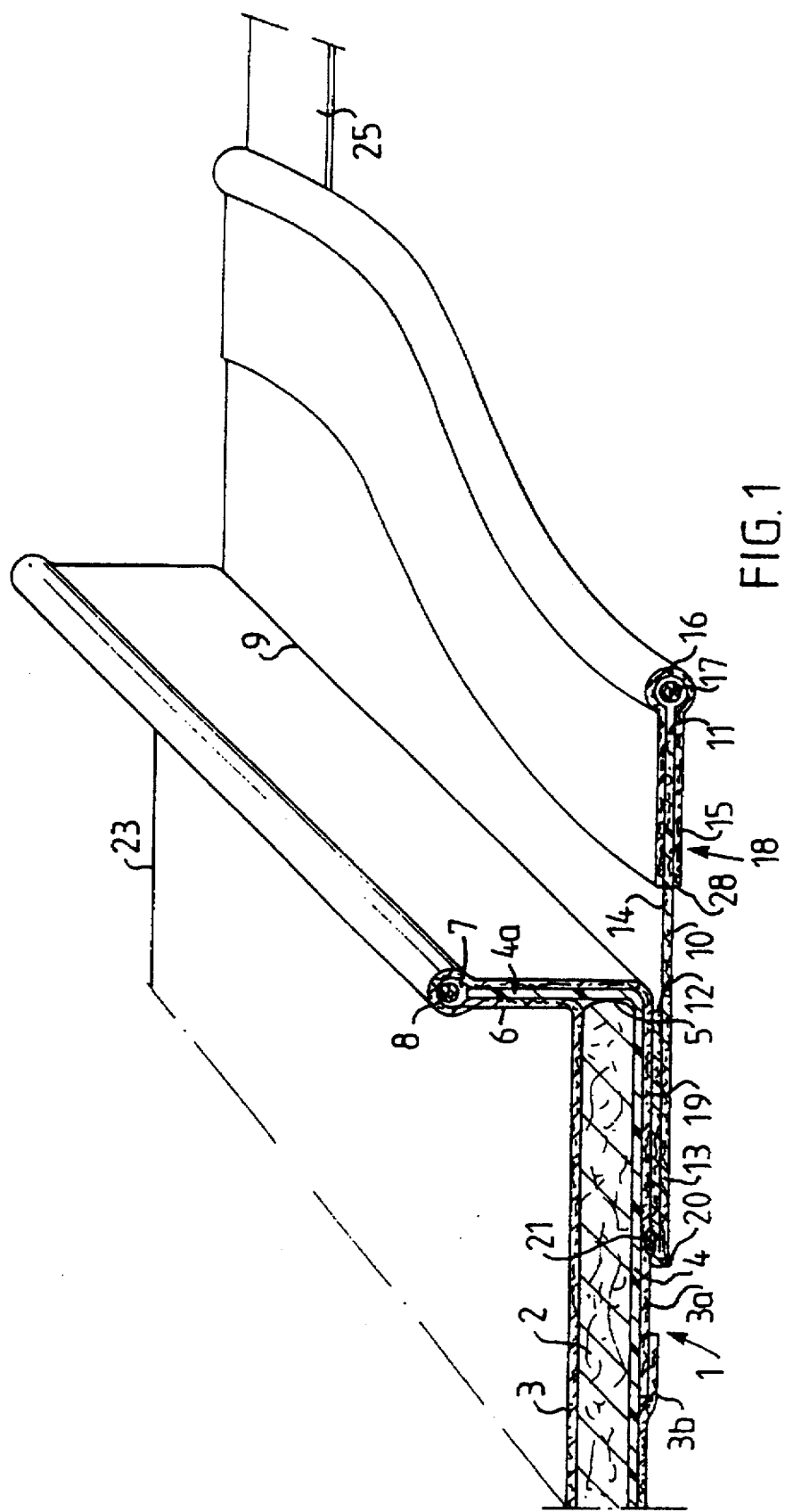
FIG. 1 is a perspective, sectional view taken on the line I—I in FIG. 2 and shows part of a disposable diaper according to a first embodiment of the invention, said diaper being shown laterally extended.
Figure 2:
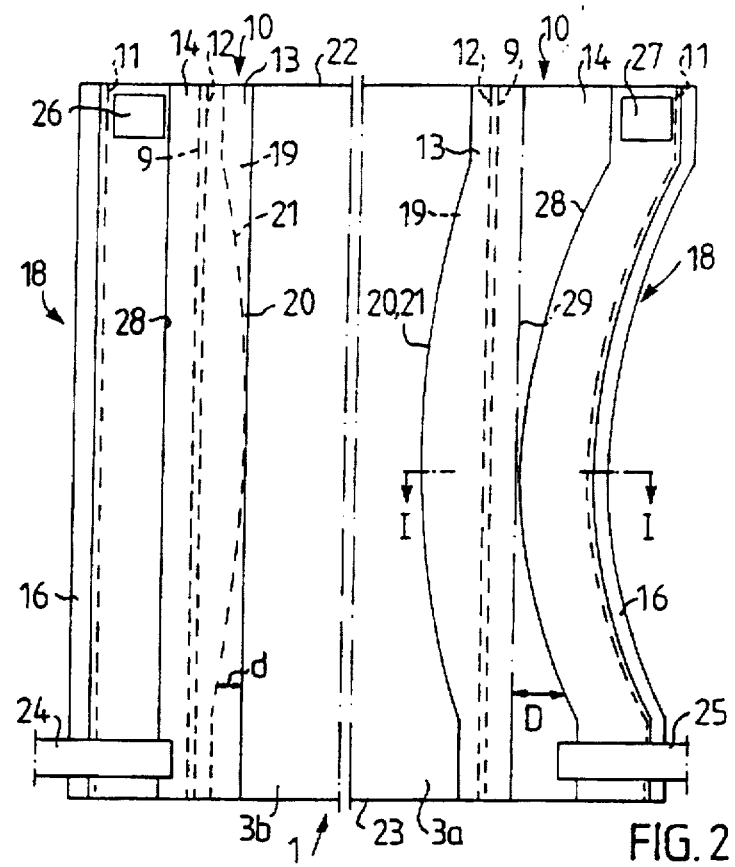
FIG. 2 illustrates that side of the diaper in FIG. 1 which lies remote from the wearer in use, said diaper being shown outstretched in its longitudinal direction to a flat state, and the left and the right halves of the Figure showing the diaper before and after being extended laterally.

In the case of the preferred embodiment illustrated in FIGS. 1 and 2, the outer casing sheet 4 is folded-up at the side-edges 5 of the absorbent body 2 and an edge-part 4a of said sheet 4 rises up over the surface of the absorbent body 2 at each edge 5. The inner casing sheet 3 is formed with a fold 6 at each of the side-edges 5 of the absorbent body, this fold embracing the upstanding edge-part 4a of the outer casing sheet 4. The inner casing sheet 3 forms above the edge-part 4a a sleeve 7 which extends in the longitudinal direction of the absorbent unit 1 and in which a pre-stretched elastic element 8, for instance a rubber thread, extends. The folds 6 form standing barriers which prevent fluid leaking laterally from the absorbent unit.

As shown in FIG. 1, the material in the inner casing sheet 3 extends from the sleeve 6 down along the outside of the edge-part 4a and a longitudinally extending edge-part 3a of said sheet 3 is folded-in beneath the absorbent body 2, outside the casing sheet 4. Correspondingly, an edge-part 3b of the casing sheet 3 is folded-in beneath the casing sheet 4 from the other edge (not shown in FIG. 1) of the absorbent unit 1. The edge-parts 3a, 3b overlap and are joined together on the underside of the absorbent unit 1. The edge-pans thereby form outside the outer casing sheet 4 a further outer or external casing sheet which comprises the same material as the inner casing sheet 3, whereby the diaper obtains an improved, unitary appearance and its outside is more pleasant to the touch. However, it is not necessary for the inner casing sheet 3 to extend down along the full outer side of the fold 6, and the fold configuration illustrated in FIG. 3, in which the outer casing sheet 4 is exposed on the outer surface of the diaper, can be used alternatively in the inventive diaper embodiment illustrated in FIGS. 1 and 2.

The fold lines between the lower part of the fold 6 and the edge-parts 3a, 3b, or the outer casing sheet 4 when no edge-pans 3a, 3b are present, are straight and parallel and form long sides 9 of the absorbent unit 1, which in the preferred embodiment has a rectangular shape.

An elongated strip 10 of skin-friendly sheet material, for instance a breathable, vapour-permeable fibre material, so-called nonwoven material, having straight, parallel side-edges 11, 12 is placed adjacent each of the long sides 9 of the absorbent unit 1. A first part 13 of the width of the strip 10 is located on the outside of the external casing sheet 3a, 3b. The other, remaining part 14 of the width of the strip 10 is located laterally outside the side-edge 9 of the absorbent unit 1. Edge elastic or leg elastic is mounted along the outer edge 11 of the strip 10 in the form of a band 15, preferably elastic material such as rubber, plastic foam, elastic nonwoven material or the like. The band 15 is folded around the side-edge 11 and is fastened to both surfaces of the strip 10 adjacent the edge 11, for instance glued thereto. The band 15 may form outside the side-edge 11 a sleeve-like fold 16 in which an elongated elastic element 17 can be mounted in a pre-stretched state. The outer part 14 of the strip 10 and the band 15 together form a diaper side-flap 18 which is located outside the absorbent unit 1.

That part 19 of the first strip part 13 that lies nearest the inner side-edge 12 of the strip 10 is folded back through 180° about a fold line 20 which, in the idle or rest state of the diaper, extends parallel with the side-edge 12 of the strip 10. This is shown in the left-hand part of FIG. 2. The backwardly-folded part 19 is positioned between the remainder of the strip-part 13 and the external casing sheet 3a, 3b and is joined thereto, for instance glued or welded thereto, along a fastening line 21 spaced from the side-edge 12. As will be seen from the left side of FIG. 2, the fastening line 21 is curved such that its distance d from the fold line 20 is smallest at the transverse centre line of the diaper and greatest at the front and rear waist edges 22 and 23 of the diaper.

The diaper is provided with self-gripping tapes or burr fasteners, 24, 25 on its rear waist-edge 23. When the diaper is to be put on, the self-gripping tapes 24, 25 are gripped on both sides of the absorbent unit 1 and pulled apart and then passed around the wearer's waist and fastened across the wearer's stomach, so as to form a waistband 24, 25. The front end-edge of the diaper is moved up over the stomach and the front corners of the diaper are gripped and pulled apart. The corners, i.e. the ends of the side-flaps 18, adjacent the front waist-edge 22 are provided with self-gripping strips 26, 27 which are complementary to the tapes 24, 25, such as to enable the strips to be fastened to the tapes. The waistband and the self-gripping tapes may be of an earlier known kind and are consequently not shown or described in detail in this document.

As the side-flaps 18 are pulled apart laterally in the aforesaid manner, when putting on the diaper, the inner part 13 of the strip 10 and the fold line 20 move laterally outwards towards the side-edge 9 of the absorbent unit 1. The movement of each point along the fold line 20 is arrested when said point reaches the fastening line 21. Since the inner part 13 of the strip 10 is folded double, the maximum distance D moved by each point along the fold line 20, and therewith each point along the outer-edge 16 of the side-flaps 18, is equal to twice the aforesaid distance d between the fastening line 21 and the fold line 20 at said point. To illustrate this, that edge of the band 15 which is located on the outside of the outer part 14 of the strip 10 is referenced 28. Indicated with a chain line 29 in the right-hand part of FIG. 2 is the position of said edge 28 when the diaper is extended longitudinally but not laterally, corresponding to the full straight line 28 shown in the left-hand part of FIG. 2. The aforesaid maximum movement path D is corresponded by the distance between the lines 28 and 29, wherein D=2d for each line transversely across the diaper.

Figure 4:
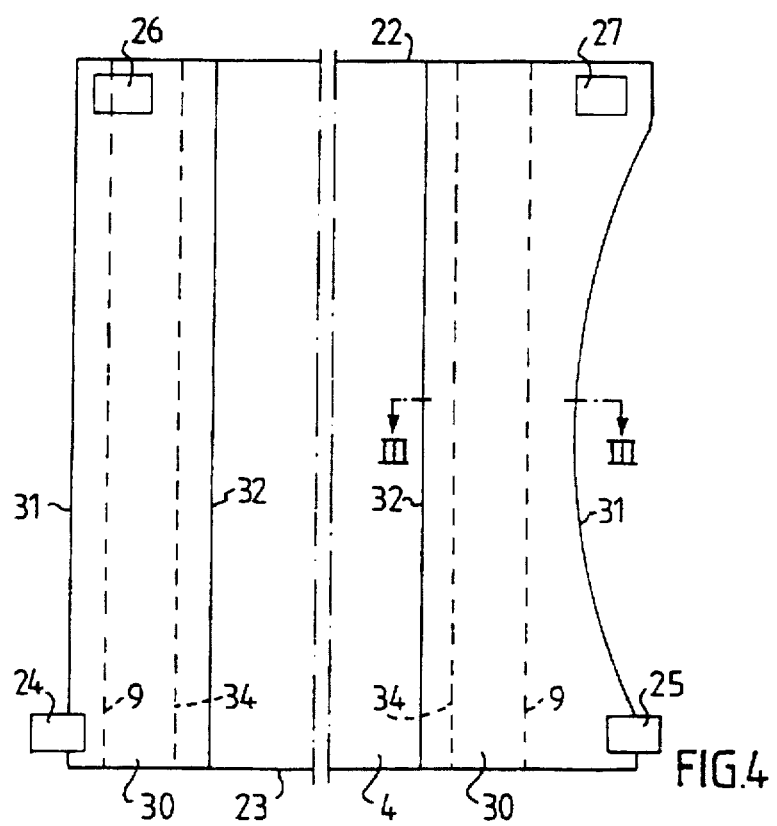
FIGS. 3 and 4 illustrate a second embodiment of the invention in a manner similar to FIGS. 1 and 2.

The absorbent unit 1 of the exemplifying embodiment illustrated in FIGS. 3 and 4 is also provided with leakage barriers formed by folds 6 having an elastic element 8 mounted in an upper sleeve 7. In the case of the FIG. 3 embodiment, however, the inner casing sheet 3 is not drawn down along the full height of the fold 6 on the outside of the upstanding edge-part 4a of the outer casing sheet 4 as in the case of the FIG. 1 embodiment, but terminates with a narrow edge-part 3c which extends down from the sleeve 7 through only a part of the height of the fold 6 and is joined, for instance glued, to the outside of the edge-part 4a.

In the case of the embodiment illustrated in FIGS. 3 and 4, the strips 30 are made of an elastic or plastically deformable material and in their rest state have parallel edges 31, 32. A first part 33 of the width of each strip 30 extends over the outside of the outer casing sheet 4 and is fastened thereto by means of a glue bead or a weld join 34, which extends in a straight line parallel with the edge 32 of the strip. The other parts 35 of the strips 30 located outside the long sides 9 of the absorbent unit 1 form the diaper side-flaps 36, which in this case are totally formable.

Because the side-flaps 36 are made of an elastic or formable material, the side-flaps will lie conformingly against the wearer's legs when extended, and therewith hold the absorbent unit 1 in the desired position. However, the side-flaps 36 may also be provided with further, separate edge elastic when so desired, for instance an elastic thread along the outer edge 31 of the strip 30.

When manufacturing diapers or absorbent articles in accordance with the invention, the absorbent unit 1 is first produced separately per se and the strips 10 or 30 forming the respective side-flaps 18, 36 are also produced separately per se. When the side-flaps are to have separate edge-elastics 15–17, these elastics are mounted at this stage of the manufacturing process. The first, inner parts 13, 33 of respective strips 18, 36 are then joined, glued or welded, to the outer casing sheet 4 of the absorbent body 1, either along a curved fastening line according to FIGS. 1 and 2, or along a straight fastening line according to FIGS. 3 and 4.

When manufacturing absorbent articles according to FIGS. 1 and 2, an absorbent unit is produced by enclosing absorbent material between a moving web of liquid-permeable sheet material 3 and a moving web of liquid-impermeable sheet material 4. The folds 6 which form the longitudinally extending side-leakage barriers are formed at the same time in this stage of manufacture, if so desired.

Separate from the manufacture of the absorbent unit 1, there are formed from sheet material two moving side-flap webs 10 which are provided with edge elastic 15, 17. The two side-flap webs and the absorbent-unit web are then brought together. A first part 13 of the width of the web located adjacent the side-edge of each side-flap web 10 is folded double around a straight longitudinally extending fold line 20, see the left-hand part of FIG. 2. The backwardly-folded part 19 is joined to the outer or external casing sheet 3a, 3b or 4 of the absorbent-unit web 1 along a longitudinally extending fastening line 21, wherein the distance of the fastening line 21 from the longitudinally extending side-edge 9 of the absorbent-unit web 1 is varied during manufacture, so that the fastening line 21 becomes curved. That part of the side-flap web-part 13 which is not folded back extends from the fold line 20 towards and beyond the longitudinally extending side-edge 9 of the absorbent-unit web 1 and there merges with a second, remaining width-part 14 of the side-flap web 10, which thus lies laterally outside said side-edge 9.

Separate absorbent articles are cut from the thus produced, moving article web, by cutting the web transversely.

I claim:

1. An absorbent article having an elongated absorbent unit, comprising:

a liquid-permeable first, inner casing sheet which forms part of a side of the article which lies proximal to the wearer in a worn state of the article;

a liquid-impermeable second, outer casing sheet; and an elongated absorbent body enclosed between said first and second casing sheets;

the absorbent unit having two opposing long sides;

the absorbent article further having along each of said long sides a side-flap which is made of a strip of soft sheet material whose length is greater than its width, and which is separate from but joined to one of said casing sheets and an outer contour of the side flap facing away from the absorbent unit is curved in the worn state of the article;

each of said strips has a longitudinally extending first part forming a portion of the width of the strip located adjacent the absorbent unit, and a longitudinally extending second part forming a remaining width of the strip located laterally outside the long side of the absorbent unit;

the first strip part extends in across the adjacent long side of the absorbent unit and is joined to the absorbent unit;

the second strip part is extendible in a transverse direction of the strip from a first state assumed when the article is unused to a second state assumed when the article is worn; and wherein in said first state the outer contour of said second strip part, and thus the side flap, is a substantially straight line, whereas in said second state the transverse extension of the second strip part varies along a length of the strip so that the strip obtains said curved outer contour along at least a center portion of the article.

2. The article according to claim 1, wherein the absorbent unit is essentially rectangular and has parallel long sides.

3. The article according to claim 1, wherein adjacent to and along each of the long sides of the absorbent unit, there is formed in the inner casing sheet an upstanding fold which encloses at least partially a similar upstanding edge-part of the outer casing sheet; and an elongated elastic element is mounted in the fold in a prestretched state outside said upstanding edge-part.

4. The article according to claim 1, wherein said first part of the strip presents a part which is folded back through 180° so as to be located between a remaining portion of the first of the strip and adjacent casing sheet; and the backwardly-folded part of the strip is joined to the adjacent casing sheet along a fastening line which extends generally along the side-edge of the strip and is curved in accordance with a desired outer contour of the side-flap of the article.

5. The article according to claim 4, wherein the strips forming the side-flaps extend over said second casing sheet and with their backwardly folded parts joined thereto.

6. The article according to claim 4 wherein each strip has straight, parallel side-edges when the article is extended longitudinally.

7. The article according to claim 4, wherein the side-edges of said second parts of the strips are provided with elastic elements therealong.

8. The article according to claim 7, wherein the elastic elements include elastic bands mounted adjacent said side-edges on at least one of the two surfaces of the strip.

9. The article according to claim 3, wherein said strips are fastened to said outer casing sheet along a straight fastening line.

10. The article according to claim 9, wherein the strips are comprised of deformable material.

11. The article according to claim 9, wherein the strips are comprised of elastic material.

12. A method of manufacturing an absorbent article, comprising:

enclosing an absorbent material between a moving web of liquid-permeable sheet material to form an inner casing sheet, and a moving web of liquid-impermeable sheet material to form an outer casing sheet;

thereafter mutually joining said webs to form an absorbent-unit web;

forming two moving side-flap webs from sheet material;

joining the side-flap webs to the absorbent unit web; and cutting the thus formed combination of moving, mutually joined side-flap and absorbent unit webs transversely, such as to form separate absorbent articles;

arranging a first part of a width of each of said side-flap webs adjacent a longitudinally extending side-edge of the absorbent unit web over a portion of the absorbent material and joining said first web part to the absorbent unit within this portion; and arranging a remaining, second part of the width of the side-flap web laterally outside the absorbent-unit web such as to form side-flaps.

13. The method according to claim 12, further comprising folding said first part of the width of each side-flap web double along a fold line;

joining the backwardly folded part of said first web part to the absorbent unit web along a curved fastening line extending generally in a longitudinal direction of the web; and arranging that part of said second web part which is not folded back on that side of said backwardly folded part which lies remote from the absorbent unit web such that said part will extend from the fold line towards the side-edge of the absorbent unit web and there merge with said second part of the width of the side-flap web.

14. The method according to claim 12, further comprising mounting elongated elastic elements along the side-edges of said second width-parts of the side-flap webs and thereafter joining the first width-parts of the side-flap webs with the absorbent-unit web.

15. An absorbent article having an elongated absorbent unit, comprising:

a liquid-permeable first, inner casing sheet which forms a part of a side of the article which lies proximal to the wearer in a worn state of the article;

a liquid-permeable second, outer casing sheet; and an elongated absorbent body enclosed between said first and second casing sheets;

the absorbent unit having two opposing long sides;

the absorbent article further having along each of said long sides a side-flap which is made of a strip of sheet material whose length is greater than its width, and which is separate from but joined to one of said casing sheets;

each of said strips includes a first part that is folded backwardly along a fold line and arranged between the absorbent unit and a second part of the strip, the fold line being substantially parallel to a longitudinal direction of the absorbent unit;

each of said strips being fastened to said absorbent unit by means of a curved fastening line that fastens said first part to the absorbent unit, wherein the fastening line is closest to the fold line at a center of said absorbent unit and extends away from the absorbent unit at ends of the absorbent unit.

* * * * *